(12) United States Patent
Danilo

(10) Patent No.: US 8,053,602 B2
(45) Date of Patent: Nov. 8, 2011

(54) PRODUCTION OF PROPIONIC ACID

(75) Inventor: Zim Danilo, Campinas (BR)

(73) Assignee: Rhodia Poliamida E Especialidades Ltda, Sao Paulo SP (BR)

( * ) Notice: Subject to any disclaimer, the term of this patent is extended or adjusted under 35 U.S.C. 154(b) by 156 days.

(21) Appl. No.: 12/525,733

(22) PCT Filed: Jan. 30, 2008

(86) PCT No.: PCT/IB2008/000287
§ 371 (c)(1),
(2), (4) Date: Jan. 22, 2010

(87) PCT Pub. No.: WO2008/096256
PCT Pub. Date: Aug. 14, 2008

(65) Prior Publication Data
US 2010/0137640 A1 Jun. 3, 2010

(30) Foreign Application Priority Data

Feb. 5, 2007 (FR) ..................................... 07 00788

(51) Int. Cl.
*C07C 51/00* (2006.01)
(52) U.S. Cl. ...................................................... 562/538
(58) Field of Classification Search ........................ None
See application file for complete search history.

(56) References Cited

U.S. PATENT DOCUMENTS

| 2,874,187 | A | | 2/1959 | Ohsol et al. | |
| 7,612,230 | B2 | * | 11/2009 | Shima et al. | 562/535 |
| 7,910,771 | B2 | * | 3/2011 | Dubois et al. | 562/532 |

* cited by examiner

*Primary Examiner* — Karl J Puttlitz
(74) *Attorney, Agent, or Firm* — Buchanan Ingersoll & Rooney, P.C.

(57) ABSTRACT

Propionic acid is produced via the catalytic dehydration of glycerol in the presence of at least one transition metal catalyst.

13 Claims, No Drawings

PRODUCTION OF PROPIONIC ACID

CROSS-REFERENCE TO PRIORITY/PCT APPLICATIONS

This application claims priority under 35 U.S.C. §119 of FR 0700788, filed Feb. 5, 2007, and is a continuation/national phase of PCT/IB 2008/000287, filed Jan. 30, 2008 and designating the United States (published in the French language on Aug. 14, 2008, as WO 2008/096256 A2; the title and abstract were also published in English), each hereby expressly incorporated by reference in its entirety and each assigned to the assignee hereof.

The present invention relates to a method for manufacturing propionic acid by catalytic dehydration of glycerol.

Novel techniques for the production of biodiesel have been greatly developed in recent years. This renewable fuel reduces environmental pollution, and makes it possible to generate possibilities of jobs in geographical regions that are less favorable to other economic activities, thus promoting social insertion and development. In general, biodiesel is produced by the transesterification of glycerides by short-chain alcohols, for example methanol or ethanol. This method generates glycerol as one of the main by-products.

The transesterification reaction is catalyzed by an acid or a base, depending on the characteristics of the oils and/or of the greases used. After the transesterification reaction, the resulting esters are separated from the excess reactants, from the catalyst and from the by-products via a two-step process. Firstly, the glycerol is separated by settling or centrifugation, then, the soaps, catalyst residues and alcohol residues are removed by washing with water and sparing or using magnesium silicate with filtration.

Sizable production of biodiesel is accompanied by a high production of glycerol which is obtained as a by-product.

Thus, there is a need to develop methods or applications for reusing the glycerol thus produced.

Glycerol, also known as glycerin or 1,2,3-propanetriol is an organic compound that contains three hydroxyl functional groups and has an alcohol function. Its structure is represented in the following formula (I):

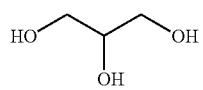

FORMULA (I)

Glycerol is used, in particular, as a raw material for the production of several compounds. U.S. Pat. Nos. 5,387,720 and 5,426,249 describe the production of 1,3-propanediol and of acrolein from glycerol. Patent application US 2005/0244312 describes the production of hydroxyacetone and of 1,2-propanediol from glycerol. International application WO 2003/035582, and also the literature (Appl. Cat. A: General 281, 2005, 225-231; Bull. Soc. Chim. France 2, 1989, 148-155; Ind. Eng. Chem. Res. 42, 2003, 2913-2923; Green Chem. 6, 2004, 359-361; J. Cat. 240, 2006, 213-221), describe the use of glycerol as a reactant in hydrogenolysis reactions for the production of 1,2-propanediol and 1,3-propanediol. The journal *Science* (No. 300, year 2003, pages 2075-2077) also mentions the use of glycerol as a raw material for the production of hydrogen and methane.

The present invention proposes a novel application of glycerol that consists of the use of the latter as a raw material for the manufacture of propionic acid.

Propionic acid, propanoic acid or ethanecarboxylic acid is a naturally-occurring carboxylic acid. In its pure state, it is a colorless corrosive liquid that gives off a pungent odor. Its structure is represented in the following formula (II):

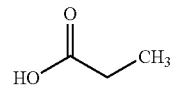

FORMULA II

Industrially, propionic acid is produced from the oxidation of propanaldehyde with air. Cobalt or manganese ions catalyze the reaction even at high temperatures. In general, the industrial processes are carried out at a temperature of 40-50° C. and employ the following reaction:

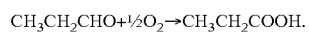

Large amounts of propionic acid have already been produced as by-products of acetic acid. However, modifications of the processes for manufacturing acetic acid have greatly reduced the production of propionic acid as a by-product.

Propionic acid is also produced biologically, from the metabolic breakdown of fatty acids having very long chains and of certain amino acids. Bacteria of the genus *Propionibacterium*, generally found in the stomachs of ruminants, produce propionic acid as the end product of anaerobic metabolism.

Propionic acid is, for example, used in the inhibition of the growth of certain fungi and of certain bacteria. Thus, propionic acid is generally used as a preservative for food intended for human or animal consumption. Propionic acid is also used in certain antifungal talcs for the feet, in the manufacture of pesticides or of pharmaceutical products.

Propionic acid may also be used as a chemical intermediate, for example for modifying synthetic cellulose fibers.

Derivatives of propionic acid also have a technical and economic advantage. Thus, for example, the ester of propionic acid may be used as a solvent of artificial flavoring.

The many industrial uses of propionic acid, and the limited number of methods that enable it to be obtained make it a more beneficial product than glycerol.

The objective of the invention is to provide that makes it possible to recycle the glycerol to propionic acid, consisting in dehydrating the glycerol.

The glycerol is advantageously obtained as a by-product of biodiesel production processes. However, the invention also applies to the recycling of the glycerol obtained from any source.

The glycerol used in the method of the invention may be pure or may contain water, for example between about 15% and about 90% by weight of water.

The dehydration is carried out in a single step, in the presence of at least one catalyst comprising a transition metal. This type of catalyst, under the conditions of the method of the present invention, procures a dehydration of the glycerol, resulting in the formation of propionic acid.

In particular, within the context of the present invention, the catalysts are chosen from one or more of the following elements: palladium, rhodium, nickel, Raney nickel, ruthenium and platinum, optionally supported on activated carbon, silica or alumina.

An appropriate concentration of the catalyst may vary between about 0.1% to about 10%, more particularly about 5% by weight.

The suitable ratio between the amount of glycerol and of catalyst (metal+support) may vary between about 5 to about 55. A suitable ratio for the method of the invention between the amounts of glycerol and of transition metal contained in the catalyst may vary between about 10 and about 1000.

The reaction may be carried out in an appropriate manner in conventional reactors, in the presence or absence of oxygen, particularly by keeping the pressure and the temperature constant throughout the duration of the reaction.

In a suitable manner, the temperature of the reaction medium is between about 180° C. and about 300° C., more particularly it is equal to about 250° C. The reaction is carried out, advantageously at a pressure between about 5 Pa and about 4000 Pa, and is more particularly still close to about 980 Pa.

The pH of the reaction medium may advantageously vary from about 2 to about 13, particularly it may be equal to about 7.

Illustrative examples of particular embodiments of the present invention will subsequently be given, without however representing a limitation other than those which are contained in the enclosed claims.

EXAMPLE 1

A stainless steel reactor having a capacity of 150 ml, equipped with a mechanical stirrer of Huston turbine type, operating at 500 rpm, was charged with 59.08 g of glycerol and 1.08 g of platinum on activated carbon as catalyst (5% Pt/C, humidity of 55.31%). The reactor was then sealed, purged with nitrogen and heated to 180° C. with stirring. As the reaction took place, the relative pressure in the reactor was maintained at 4.9 Pa.

The reaction products were collected through the gas outlet valve, equipped with a condenser followed by a trap at 0° C. (ice) and by a trap at –69° C. (dry ice). A purge after the last trap provided the outlet of the non-condensable gases.

The reaction products were characterized by gas chromatography coupled with mass spectrometry and quantified by gas chromatography with a flame ionization detector using an external standardization method. The results were expressed as the percentage of propionic acid present in all of the organic compounds condensed in the outlet stream from the reactor, without taking into account the water present in the raw material or that was optionally formed during the process. At the end of the process, 49% of glycerol had been converted and the concentration of propionic acid in the outlet stream compared to the other organic compounds was 0.98%.

EXAMPLE 2

A stainless steel reactor having a capacity of 150 ml, equipped with a mechanical stirrer of Huston turbine type, operating at 500 rpm, was charged with 59.03 g of glycerol and 10.84 g of platinum on activated carbon as catalyst (5% Pt/C, humidity of 55.31%). The reactor was then sealed, purged with nitrogen and heated to 250° C. with stirring. As the reaction took place, the relative pressure in the reactor was maintained at 980.66 Pa.

The reaction products were collected through the gas outlet valve, equipped with a condenser followed by a trap at 0° C. (ice) and by a trap at –69° C. (dry ice). A purge after the last trap provided the outlet of the non-condensable gases.

The reaction products were characterized by gas chromatography coupled with mass spectrometry and quantified by gas chromatography with a flame ionization detector using an external standardization method. The results were expressed as the percentage of propionic acid present in all of the organic compounds condensed in the outlet stream from the reactor, without taking into account the water present in the raw material or that was optionally formed during the process. At the end of the process, 90% of glycerol had been converted and the concentration of propionic acid in the outlet stream compared to the other organic compounds was 1.19%.

EXAMPLE 3

A stainless steel reactor having a capacity of 150 ml, equipped with a mechanical stirrer of Huston turbine type, operating at 500 rpm, was charged with 59.11 g of glycerol and 1.20 g of platinum on activated carbon as catalyst (5% Pt/C, humidity of 55.31%). The reactor was then sealed, purged with nitrogen and heated to 250° C. with stirring. As the reaction took place, the relative pressure in the reactor was maintained at 980.665 Pa.

The reaction products were collected through the gas outlet valve, equipped with a condenser followed by a trap at 0° C. (ice) and by a trap at –69° C. (dry ice). A purge after the last trap provided the outlet of the non-condensable gases.

The reaction products were characterized by gas chromatography coupled with mass spectrometry and quantified by gas chromatography with a flame ionization detector using an external standardization method. The results were expressed as the percentage of propionic acid present in all of the organic compounds condensed in the outlet stream from the reactor, without taking into account the water present in the raw material or that was optionally formed during the process. At the end of the process, 100% of glycerol had been converted and the concentration of propionic acid in the outlet stream compared to the other organic compounds was 0.82%.

EXAMPLE 4

A stainless steel reactor having a capacity of 150 ml, equipped with a mechanical stirrer of Huston turbine type, operating at 500 rpm, was charged with 59.99 g of glycerol and 1.37 g of platinum on activated carbon as catalyst (5% Pt/C, humidity of 55.31%). The pH of the medium was adjusted with a 50% NaOH solution up to 13. The reactor was then sealed, purged with nitrogen and heated to 210° C. with stirring. As the reaction took place, the relative pressure in the reactor was maintained at 980.665 Pa.

The reaction products were collected through the gas outlet valve, equipped with a condenser followed by a trap at 0° C. (ice) and by a trap at –69° C. (dry ice). A purge after the last trap provided the outlet of the non-condensable gases.

The reaction products were characterized by gas chromatography coupled with mass spectrometry and quantified by gas chromatography with a flame ionization detector using an external standardization method. The results were expressed as the percentage of propionic acid present in all of the organic compounds condensed in the outlet stream from the reactor, without taking into account the water present in the raw material or that was optionally formed during the process. At the end of the process, 100% of glycerol had been converted and the concentration of propionic acid in the outlet stream compared to the other organic compounds was 0.58%.

EXAMPLE 5

A stainless steel reactor having a capacity of 150 ml, equipped with a mechanical stirrer of Huston turbine type, operating at 500 rpm, was charged with 58.77 g of glycerol and 1.20 g of platinum on activated carbon as catalyst (5% Pt/C, humidity of 55.31%). The reactor was then sealed, purged with nitrogen and heated to 300° C. with stirring. As the reaction took place, the relative pressure in the reactor was maintained at 980.665 Pa.

The reaction products were collected through the gas outlet valve, equipped with a condenser followed by a trap at 0° C. (ice) and by a trap at −69° C. (dry ice). A purge after the last trap provided the outlet of the non-condensable gases.

The reaction products were characterized by gas chromatography coupled with mass spectrometry and quantified by gas chromatography with a flame ionization detector using an external standardization method. The results were expressed as the percentage of propionic acid present in all of the organic compounds condensed in the outlet stream from the reactor, without taking into account the water present in the raw material or that was optionally formed during the process. At the end of the process, 100% of glycerol had been converted and the concentration of propionic acid in the outlet stream compared to the other organic compounds was 0.87%.

EXAMPLE 6

A stainless steel reactor having a capacity of 150 ml, equipped with a mechanical stirrer of Huston turbine type, operating at 500 rpm, was charged with 57.11 g of glycerol and 6.0 g of platinum on activated carbon as catalyst (5% Pt/C, humidity of 55.31%). The reactor was then sealed, purged with nitrogen and heated to 250° C. with stirring. As the reaction took place, the relative pressure in the reactor was maintained at 980.665 Pa.

The reaction products were collected through the gas outlet valve, equipped with a condenser followed by a trap at 0° C. (ice) and by a trap at −69° C. (dry ice). A purge after the last trap provided the outlet of the non-condensable gases.

The reaction products were characterized by gas chromatography coupled with mass spectrometry and quantified by gas chromatography with a flame ionization detector using an external standardization method. The results were expressed as the percentage of propionic acid present in all of the organic compounds condensed in the outlet stream from the reactor, without taking into account the water present in the raw material or that was optionally formed during the process. At the end of the process, 100% of glycerol had been converted and the concentration of propionic acid in the outlet stream compared to the other organic compounds was 16.22%.

The invention claimed is:

1. A process for the production of propionic acid, comprising dehydrating glycerol in the presence of at least one supported transition metal catalyst, wherein said supported transition metal catalyst comprises one or more elements selected from the group consisting of palladium, rhodium, nickel, Raney nickel, ruthenium and platinum.

2. The process for the production of propionic acid as defined by claim 1, said at least one catalyst being supported on a support selected from the group consisting of activated carbon, silicon and alumina.

3. The process for the production of propionic acid as defined by claim 1, the concentration of said at least one catalyst in the medium of dehydration ranging from 0.1% to 10% by weight.

4. The process for the production of propionic acid as defined by claim 3, the concentration of said at least one catalyst being equal to 5% by weight.

5. The process for the production of propionic acid as defined by claim 1, wherein the ratio between the amounts of glycerol and of catalyst (metal+support) ranges from about 5 to about 55, and the ratio between the amounts of glycerol and of transition metal contained in the at least one catalyst ranges from 10 to 1,000.

6. The process for the production of propionic acid as defined by claim 1, wherein the glycerol contains about 15% to about 90% by weight of water.

7. The process for the production of propionic acid as defined by claim 1, wherein the pressure and temperature of dehydration are maintained constant throughout the duration of the reaction.

8. The process for the production of propionic acid as defined by claim 1, wherein the temperature of dehydration ranges from 180° C. to 300° C.

9. The process for the production of propionic acid as defined by claim 8, wherein the temperature of dehydration is equal to 250° C.

10. The process for the production of propionic acid as defined by claim 1, wherein the pressure of dehydration ranges from 5 to 4,000 Pa.

11. The process for the production of propionic acid as defined by claim 10, wherein the pressure of dehydration is equal to 980 Pa.

12. The process for the production of propionic acid as defined by claim 1, wherein the pH of the medium of dehydration ranges from 2 to 13.

13. The process for the production of propionic acid as defined by claim 12, wherein the pH of the medium of dehydration is equal to 7.

\* \* \* \* \*